(12) United States Patent
Jang et al.

(10) Patent No.: US 10,044,951 B2
(45) Date of Patent: Aug. 7, 2018

(54) IMAGE SYSTEM

(71) Applicants: Rayence Co., Ltd., Gyeonggi-do (KR); VATECH EWOO Holdings Co., Ltd., Gyeonggi-do (KR)

(72) Inventors: Seong-Eun Jang, Gyeonggi-do (KR); Jae-Chul Kim, Gyeonggi-do (KR)

(73) Assignees: Rayence Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 0 days.

(21) Appl. No.: 15/511,633

(22) PCT Filed: Sep. 15, 2015

(86) PCT No.: PCT/KR2015/009673
§ 371 (c)(1),
(2) Date: Mar. 15, 2017

(87) PCT Pub. No.: WO2016/043498
PCT Pub. Date: Mar. 24, 2016

(65) Prior Publication Data
US 2017/0264837 A1  Sep. 14, 2017

(30) Foreign Application Priority Data

Sep. 15, 2014  (KR) .......................... 10-2014-0122205

(51) Int. Cl.
*H04N 5/357* (2011.01)
*A61B 6/14* (2006.01)
(Continued)

(52) U.S. Cl.
CPC .............. *H04N 5/357* (2013.01); *A61B 6/14* (2013.01); *H01L 27/14663* (2013.01); *H01L 31/03926* (2013.01); *H04N 5/378* (2013.01)

(58) Field of Classification Search
CPC .......... H04N 5/357; H04N 5/378; H04N 5/32; H04N 5/3696; H04N 5/2253; A61B 6/14;
(Continued)

(56) References Cited

U.S. PATENT DOCUMENTS 6,471,399 B1  10/2002  Zylka et al.
7,609,372 B1 *  10/2009  Tsai ................... G01M 11/0214
                                                                250/201.2
(Continued)

FOREIGN PATENT DOCUMENTS

JP  10-023334 A  1/1998
JP  2002-531209 A  9/2002
(Continued)

OTHER PUBLICATIONS

Korean Intellectual Property Office, International Search Report of International Application No. PCT/KR2015/009673, dated Mar. 18, 2016.
(Continued)

*Primary Examiner* — Albert Cutler
(74) *Attorney, Agent, or Firm* — IP Legal Services, LLC

(57) ABSTRACT

The present invention provides an image sensor having a flexible property, the image sensor includes multiple pixels provided in an active area where incident light is detected, the multiple pixels having a photoelectric conversion element and an image correction pattern positioned at a front of the photoelectric conversion element in a direction of an incident surface to which the light is incident, the image correction pattern being formed of a material blocking the light.

3 Claims, 4 Drawing Sheets

(51) Int. Cl.
*H01L 31/0392* (2006.01)
*H04N 5/378* (2011.01)
*H01L 27/146* (2006.01)

(58) Field of Classification Search
CPC ......... H01L 31/03926; H01L 27/14663; G01T 1/2018
USPC .......................... 348/175, 187, 188; 382/275
See application file for complete search history.

(56) References Cited

U.S. PATENT DOCUMENTS

| | | | | |
|---|---|---|---|---|
| 7,808,525 | B2* | 10/2010 | Katayama | G01C 11/02 348/175 |
| 8,290,271 | B2 | 10/2012 | Jeong et al. | |
| 8,866,913 | B1* | 10/2014 | Hsieh | H04N 17/002 348/153 |
| 2003/0031296 | A1* | 2/2003 | Hoheisel | G01T 1/2018 378/98.8 |
| 2006/0044463 | A1* | 3/2006 | Talley | H04N 5/2253 348/373 |
| 2006/0262461 | A1* | 11/2006 | Wood | A61B 6/145 361/1 |
| 2007/0040166 | A1* | 2/2007 | Kaluzhny | H01L 27/14627 257/40 |
| 2007/0164223 | A1* | 7/2007 | Hennessy | G01T 1/2018 250/361 R |
| 2009/0234183 | A1* | 9/2009 | Abe | A61B 1/00165 600/103 |
| 2010/0072379 | A1* | 3/2010 | Nishino | G01T 1/2018 250/363.08 |

FOREIGN PATENT DOCUMENTS

| | | |
|---|---|---|
| JP | 2007-295375 A | 11/2007 |
| KR | 10-2007-0099404 A | 10/2007 |
| KR | 10-2012-0098544 A | 9/2012 |

OTHER PUBLICATIONS

Korean Intellectual Property Office, Written Opinion of International Application No. PCT/KR2015/009673, dated Mar. 18, 2016.

* cited by examiner

IMAGE SYSTEM

CROSS REFERENCE TO RELATED APPLICATIONS

This application is a National Stage Patent Application of PCT International Patent Application No. PCT/KR2015/009673 (filed on Sep. 15, 2015) under 35 U.S.C. § 371, which claims priority to Korean Patent Application No. 10-2014-0122205 (filed on Sep. 15, 2014), the teachings of which are incorporated herein in their entireties by reference.

TECHNICAL FIELD

The present invention relates to an image sensor having a flexible property. More particularly, the present invention relates to an image sensor using a method of correcting image distortion, and an image system and image processing method using the same.

BACKGROUND ART

Generally, medical or industrial X-ray radiography uses a method using a film and a screen. In this case, the method is ineffective in terms of costs and time due to problems related to development and storage, etc. of radiographic films. As a solution to these problems, digital image sensors are widely used today.

In the meantime, recently, research and development of a flexible or bendable image sensor having a flexible property have been ongoing. The image sensor having a flexible property may be particularly usefully utilized when a radiography target area is indented, for example the oral cavity.

However, in a planar image radiographed by using the image sensor having a flexible property, image distortion occurs depending on the area. That is, in respect to a portion where the image sensor is bent, an image different from actual size or location may be obtained.

However, there is no a method of correcting such image distortion. Accordingly, there is a need for a correction method.

DISCLOSURE

Technical Problem

The present invention is intended to propose a method of effectively correcting distortion of an image radiographed by using an image sensor having a flexible property.

Technical Solution

In order to accomplish the above object, the present invention provides an image sensor having a flexible property, the image sensor including: multiple pixels provided in an active area where incident light is detected, the multiple pixels having a photoelectric conversion element; and an image correction pattern positioned at a front of the photoelectric conversion element in a direction of an incident surface to which the light is incident, the image correction pattern being formed of a material blocking the light.

The image correction pattern may be positioned at, at least one of a peripheral region of the active area and an inner region of the peripheral region. The image correction pattern may be provided on an image sensor panel where the photoelectric conversion element is provided. The image correction pattern may be provided on a sheet attached on a front of an image sensor panel where the photoelectric conversion element is provided. The image correction pattern positioned at the peripheral region may be arranged in at least one direction of a lateral direction and a column direction in which the multiple pixels are arranged.

In another aspect, the present invention provides an image system including: an image sensor having a flexible property, the image sensor including: multiple pixels provided in an active area where incident light is detected, the multiple pixels having a photoelectric conversion element; and an image correction pattern positioned at a front of the photoelectric conversion element in a direction of an incident surface to which the light is incident, the image correction pattern being formed of a material blocking the light; and an image processor performing image correction for an image obtained through the image sensor by matching an image correction pattern indicated on the obtained image with the actual image correction pattern.

The image processor may identify an image distortion level by comparing at least one of positions and intervals of the image correction pattern indicated on the obtained image and of the actual image correction pattern, and may correct the obtained image based on the identified image distortion level. The image correction pattern may be positioned at, at least one of a peripheral region of the active area and an inner region of the peripheral region. The image correction pattern may be provided on an image sensor panel where the photoelectric conversion element is provided. The image correction pattern may be provided on a sheet attached on a front of an image sensor panel where the photoelectric conversion element is provided.

In still another aspect, the present invention provides an image processing method including: obtaining an image by using an image sensor having a flexible property, the image sensor including multiple pixels provided in an active area where incident light is detected, the multiple pixels having a photoelectric conversion element; and an image correction pattern positioned at a front of the photoelectric conversion element in a direction of an incident surface to which the light is incident, the image correction pattern being formed of a material blocking the light; and performing, by an image processor, image correction for the obtained image by matching an image correction pattern indicated on the obtained image with the actual image correction pattern.

The performing of the image correction may include: identifying an image distortion level by comparing at least one of positions and intervals of the image correction pattern indicated on the obtained image and of the actual image correction pattern, and correcting the obtained image based on the identified image distortion level.

Advantageous Effects

According to the present invention, the image sensor having a flexible property includes the image correction pattern. Accordingly, image processing is performed by matching an image correction pattern indicated on the obtained image with the actual image correction pattern, thereby effectively correcting image distortion.

MODE FOR INVENTION

Hereinafter, embodiments of the present invention will be disclosed in detail with reference to the drawings.

Figure 1:
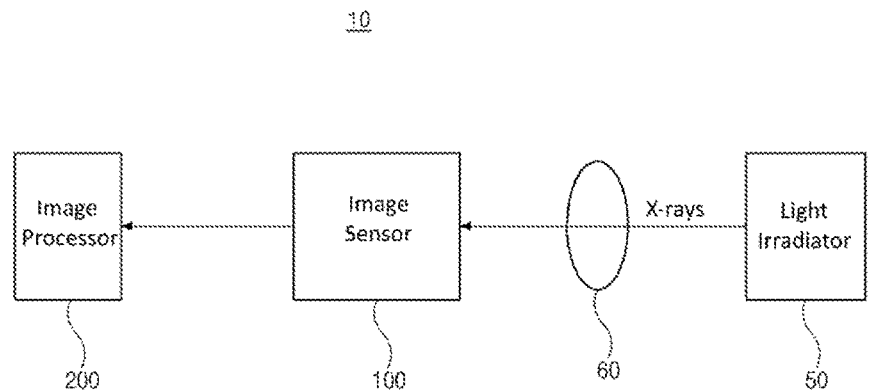
FIG. 1 is a block diagram schematically showing an image system including an image sensor according to an embodiment of the present invention.
Figure 2:
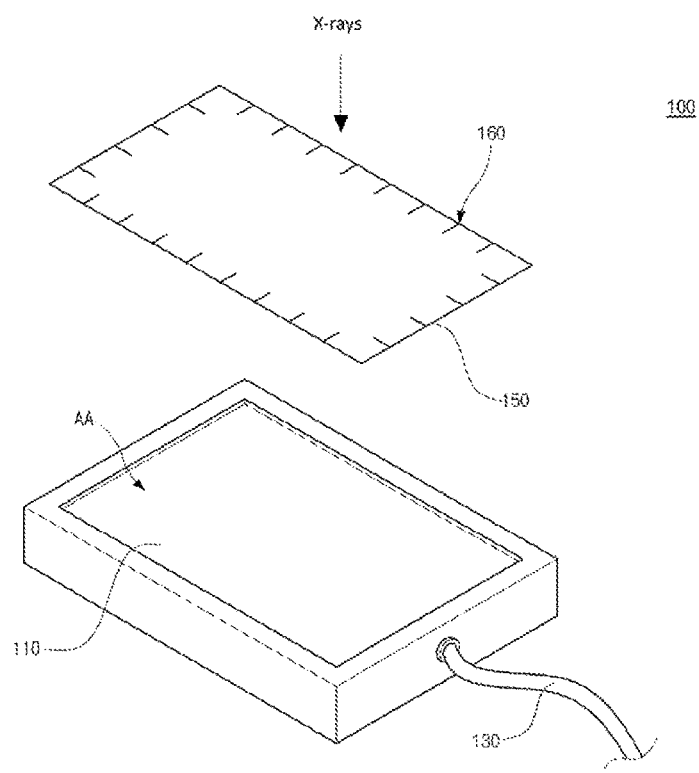
FIG. 2 is a view schematically showing an image sensor according to an embodiment of the present invention.
Figure 3:
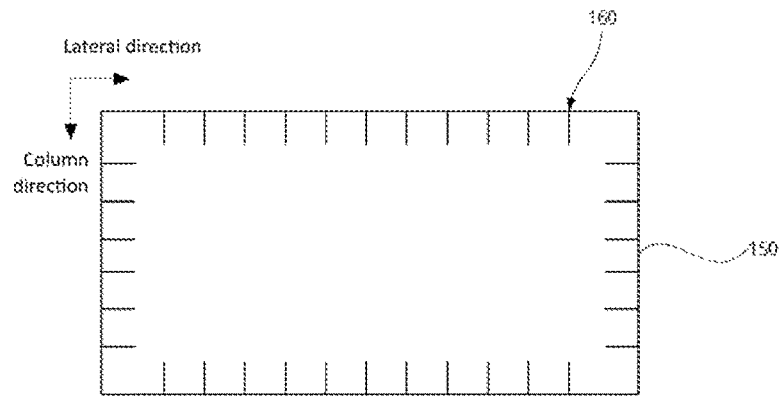
FIGS. 3 to 5 are views schematically showing examples of a sheet on which an image correction pattern of an image sensor is formed according to an embodiment of the present invention.

FIG. 1 is a block diagram schematically showing an image system including an image sensor according to an embodiment of the present invention. FIG. 2 is a view schematically showing an image sensor according to an embodiment of the present invention. FIG. 3 is a view schematically showing a sheet on which an image correction pattern of an image sensor is formed according to an embodiment of the present invention.

Referring to FIG. 1, according to an embodiment of the present invention, an image system 10 is a system generating an image by irradiating light such as X-rays, etc., and an industrial or medical image system may be used. In the embodiment of the present invention, for convenience of description, dental, particularly, an oral X-ray radiography image system 10 is used as an example.

The image system 10 may include: a light irradiator 50 generating and irradiating light such as X-rays, etc. for image radiography; an image sensor 100 detecting light that is irradiated from the light irradiator 50 and passes through a subject 60; and an image processor 200 for obtaining an image by receiving image data from the image sensor 100 and processing the image data.

The image sensor 100 has a flexible property. As described above, by using the image sensor 100 having a flexible property, X-ray radiography for an indented target may be effectively performed, and particularly, irritation or discomfort of patients may be minimized during oral radiography.

The image sensor 100 is composed of an image sensor panel 110 where a photoelectric conversion element such as a photodiode is provided on a substrate; and a driving circuit for driving the image sensor panel.

In the image sensor panel 110, multiple pixels are arranged in matrix in a lateral direction and a column direction at an effective region for obtaining an image, namely, an active area. The photoelectric conversion element such as a photodiode is provided at each pixel so as to convert incident light into an electrical signal.

In the meantime, as the image sensor 100, a direct conversion-type sensor directly converting an incident X-ray into an electrical signal or an indirect conversion-type sensor converting an incident X-ray into visible light and converting the visible light into an electrical signal may be used.

Here, when the indirect conversion-type sensor is used, scintillators for converting an X-ray into visible light may be provided on a light incident surface of the image sensor panel 110.

The driving circuit of the image sensor 100 reads out electrical signals accumulated at the pixels, namely, image data. The read out image data is output to the image processor 200 via a transmission wire 130.

In the meantime, a sheet 150 having the image correction pattern 160 may be attached on an incident surface of the image sensor 100, namely, on a front surface of the image sensor panel 110. Here, the sheet 150 may be configured to have a detachable property.

For the sheet 150 having the image correction pattern 160, for example, silicone may be used as a material having a soft property, but without being limited thereto.

The image correction pattern 160 formed on the sheet 150 is formed of a material blocking X-rays, for example, barium sulfate may be used as a substance harmless to the human body, but without being limited thereto.

The image correction pattern 160, as seen from a plane view, is formed in respect to the active area AA of the image sensor 100, whereby the image correction pattern 160 exists on a radiographic image.

In the meantime, the image correction pattern 160 may be formed at, at least part of the sheet 150. For example, as shown in FIG. 3, the image correction pattern may be formed along a peripheral region of the sheet 150. Here, in terms of enhancing accuracy of image correction, it is desired to arrange the image correction pattern 160 at four peripheral regions positioned at the upper, lower, left, and right side of the sheet in a lateral direction and a column direction, but without being limited thereto, and may be formed at a part of the four peripheral regions.

Figure 4:
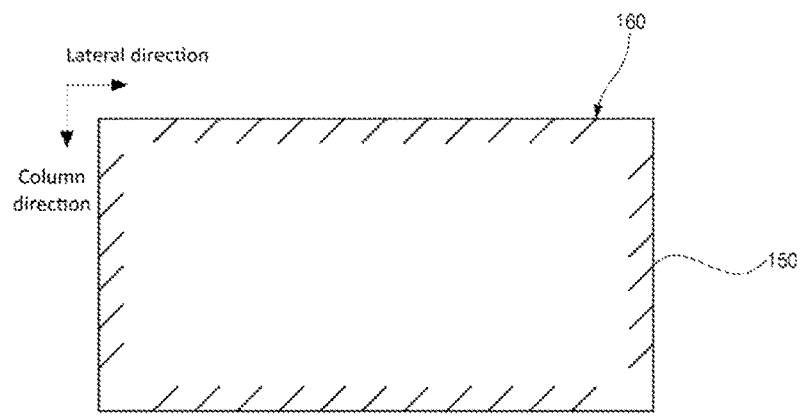

In the meantime, the image correction pattern 160 may be formed as a straight line perpendicular to an outer side of the sheet 150, but without being limited thereto. For example, as shown in FIG. 4, the image correction pattern 160 may be formed as a straight line inclined to an outer side of the sheet 150.

Figure 5:
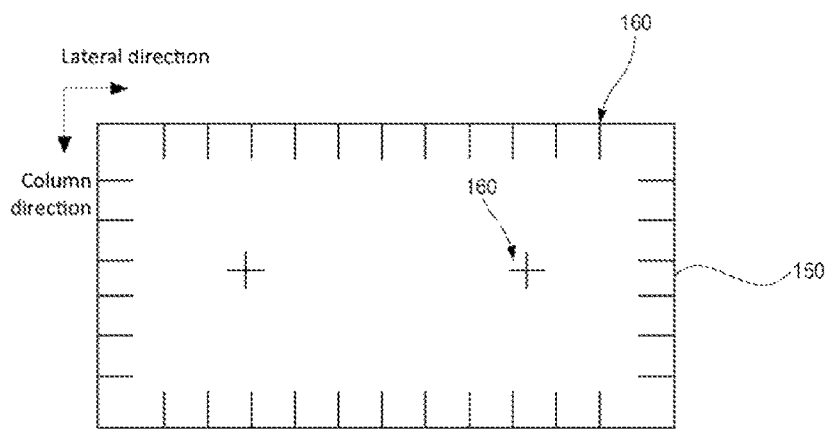

As another example, the image correction pattern 160, as shown in FIG. 5, may be formed at the peripheral regions of the sheet 150 and an inner region of the peripheral regions. As described above, when the image correction pattern 160 is formed at the inner region, accuracy of image correction for the inner region may be enhanced. Here, when the image correction pattern 160 is formed at the inner region, the image correction pattern may be formed as a crossed shape, but without being limited thereto.

As described above, the image correction pattern 160 may be arranged at various positions, and in terms of enhancing accuracy of image correction, it is desired to form the image correction pattern 160 at several regions.

In addition, the image correction pattern 160 may be arranged to be spaced apart at predetermined intervals, but without being limited thereto. In terms of enhancing accuracy of image correction, it is desired to arrange the intervals of the image correction pattern 160 to be narrow.

In the meantime, the image correction pattern 160 is formed on the sheet 150 in the above description, but may be directly formed on the image sensor panel 110 as another example.

Figure 6:
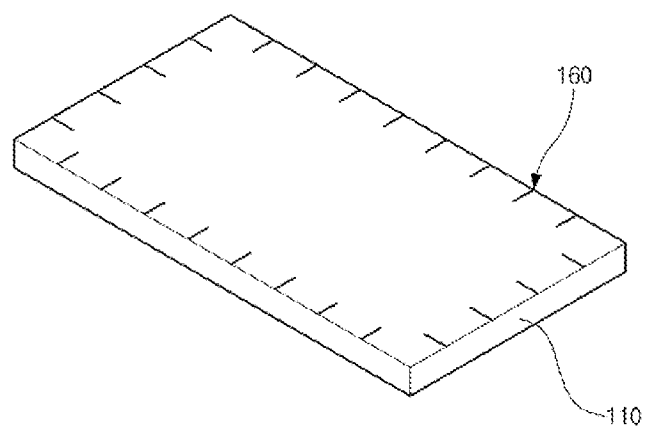
FIG. 6 is a view schematically showing an image sensor panel on which an image correction pattern of an image sensor is formed according to an embodiment of the present invention.

In this case, the image correction pattern 160, as seen from a cross section, may be formed at any positions of a front of the photoelectric conversion element in a direction of the light incident surface. For example, as shown in FIG. 6, the image correction pattern may be formed at the front most surface of the image sensor panel 110. Furthermore, the image correction pattern may be formed at the inside of the image sensor panel 110, for example, may be formed at inner and outer surfaces of a substrate, etc. in a direction of the light incident surface of the image sensor panel 110.

As described above, in the image sensor 100, the image correction pattern 160 is positioned at the front of the photoelectric conversion element in a direction of the incident surface, and may be applied to a radiographic image.

As described above, image radiography is performed by using the image sensor 100 having the image correction pattern 160, whereby the image correction pattern exists in the radiographic image, and image correction is performed for the image by the image processor 200.

Figure 7:
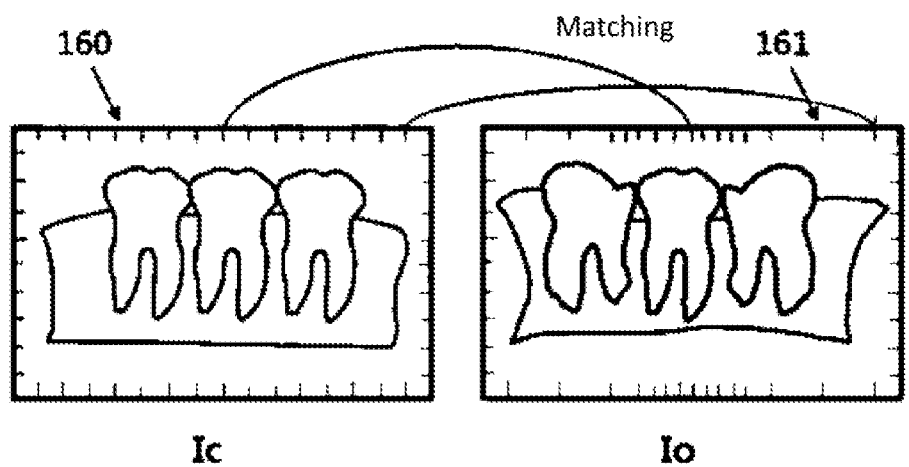
FIG. 7 is a view schematically showing a process of performing image correction by matching an actual image correction pattern with an image correction pattern indicated on an image obtained according to an embodiment of the present invention.

Referring to FIG. 7, in using the image sensor 100 having a flexible property, image radiography may be performed based on a radiography environment while the image sensor 100 is bent. In this case, distortion occurs in the obtained image (Io). Such distortion occurrence level may be identified through an image correction pattern 161 indicated on the obtained image (Io). That is, due to the bending of the image sensor 100, the positions or intervals of the image correction pattern 160 provided on the image sensor are changed and are indicated on the image (Io), whereby through the change in the positions or intervals of the image correction pattern 161 indicated on the image (Io), the distortion level of the relevant portion may be identified.

For the distorted image (Io), the image processor 200 compares the image correction pattern 161 indicated on the relevant image (Io) with the actual image correction pattern 160 that is a standard so as to identify the distortion level of the relevant portion and to correct the distortion.

As described above, the image processor 200 may obtain a corrected image (Ic) by matching the image correction pattern (161) indicated on the radiographic image (Io) with the actual image correction pattern 160.

In the meantime, the image processor 200 outputs the corrected image (Ic) to a display device such as a monitor, and accurate diagnosis is performed by using the distortion-corrected image (Ic).

Figure 8:
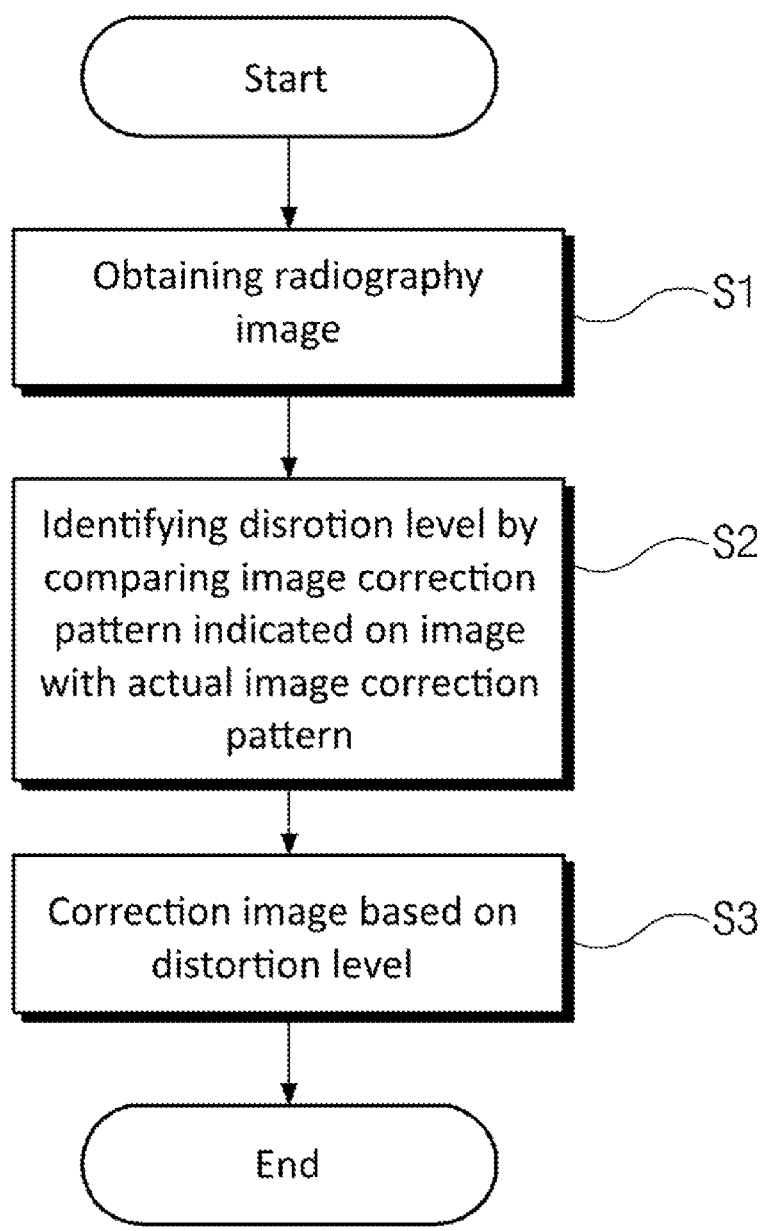
FIG. 8 is a flowchart image correction pattern showing an image processing method according to an embodiment of the present invention.

An image processing method using the above-disclosed image correction pattern will be disclosed with reference to FIG. 8.

First, X-ray image radiography is performed to obtain an image (Io) by using the image sensor 100 having the image correction pattern 160 at step S1.

Next, a distortion level for each location of the image (Io) is identified by comparing the image correction pattern 161 indicated on the obtained image with the actual image correction pattern 160 at step S2. That is, based on the change level of the positions and/or intervals of the indicated image correction pattern 161, the change in the position and/or size of the relevant image portion is identified.

Next, correction for the image is performed through the identified distortion level, and thus a corrected image (Ic) is obtained at step S3.

As described above, for an image obtained through the image sensor having a flexible property, image processing is performed by using the image correction pattern, thereby effectively correcting image distortion.

The invention claimed is:

1. An image system comprising:
an image sensor having a flexible property, the image sensor including: multiple pixels provided in an active area where incident light is detected, the multiple pixels having a photoelectric conversion element; and an image correction pattern positioned at a front of the photoelectric conversion element in a direction of an incident surface to which the light is incident, the image correction pattern being formed of a material blocking the light; and
an image processor performing image correction for an image obtained through the image sensor by matching an image correction pattern indicated on the obtained image with the actual image correction pattern,
wherein the image correction pattern is provided on an image sensor panel where the photoelectric conversion element is provided.

2. The image system of claim 1, wherein the image processor identifies an image distortion level by comparing at least one of positions and intervals of the image correction pattern indicated on the obtained image and of the actual image correction pattern, and corrects the obtained image based on the identified image distortion level.

3. The image system of claim 1, wherein the image correction pattern is positioned at, at least one of a peripheral region of the active area and an inner region of the peripheral region.

* * * * *